United States Patent [19]

Guigné

[11] Patent Number: 4,924,449

[45] Date of Patent: May 8, 1990

[54] ACOUSTIC SUB-SURFACE INTERROGATOR

[75] Inventor: Jacques Y. Guigné, St. John's, Canada

[73] Assignee: Nordco Limited, St. John's, Canada

[21] Appl. No.: 337,648

[22] Filed: Apr. 13, 1989

[51] Int. Cl.$^5$ ............................................... G01S 15/00
[52] U.S. Cl. ...................................... 367/104; 367/92; 367/138
[58] Field of Search ................. 367/104, 103, 138, 92, 367/902, 61

[56] References Cited

PUBLICATIONS

Stanic et al., A High-Frequency, Shallow-Water Acoustic Measurement System, 7-1988, pp. 155-162.
Nacci et al., Correlation of Geotechnical and Acoustical Properties of Ocean Sediments, 8-24-1988, pp. 1, 2, 270-278.
Pullin et al., Techniques Applied to Obtain Very High Resolution 3-D Seismic Imaging at an Athabasca Tar Sands Thermal Pilot, 12-1987, pp. 10-16.
Fish et al., Mapping of Submerged Shipwrecks, 2-1988, pp. 10-14.

*Primary Examiner*—Thomas H. Tarcza
*Assistant Examiner*—Daniel T. Pihulic
*Attorney, Agent, or Firm*—Fetherstonhaugh & Co.

[57] ABSTRACT

A positionable transducer array on a stationary platform proximate a layered site on the seabed coherently insonifies locations at the site with a signal having a selected power, resultant center frequency, beamwidth, bandwidth, shape and incident angle. A positionable receiver array on the platform captures the return signals. Sub-surface acoustical properties of the location are then predicted from the return signals and a calculation of the speed of sound in water at the site. Subsequent locations at the site are then interrogated and an interpolation is made of acoustical properties between locations to develop a model of the acoustical properties at the site.

11 Claims, 9 Drawing Sheets

Acoustic Core Layers

Qualitative 3-Dimensional Distribution
of Thickness-Pseudo Glacial Till Layer

| Velocity Indices [%] | | Comparison Types | Deviation S [m/s] | Ave. Velocity [m/s] |
|---|---|---|---|---|
| $\psi_{c,1}$ | 16.9 | Outer ring only | 35.9 | 1983.9 |
| $\psi_{c,2}$ | 33.1 | Inner ring only | 22.1 | 1968.4 |
| $\psi_{c,3}$ | 32.6 | Between outer & inner rings | 22.4 | n/a |
| $\psi_{c,4}$ | 22.4 | Acoustic core: outer+inner | 29.9 | 1976.2 |
| $\psi_{c,5}$ | 69.3 | 0° and 3° transmissions | 7.3 | n/a |
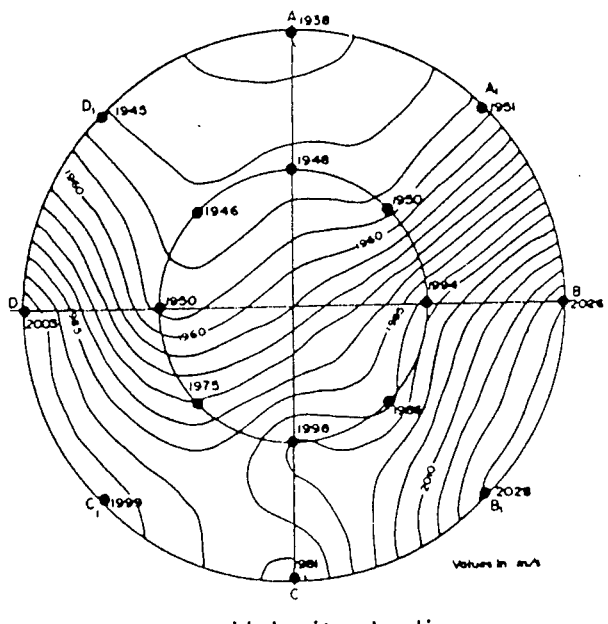
FIG. 6c     Velocity Isolines

ATTENUATION COEFFICIENT (κ)
| Attenuation Indices [%] | Comparison Types | Deviation S [dB/m-kHz] | Ave. Attenuation [dB/m-kHz] |
|---|---|---|---|
| $\psi_{a,1}$ 15.7 | Outer ring only | 0.074 | 0.24 |
| $\psi_{a,2}$ 37.7 | Inner ring only | 0.039 | 0.25 |
| $\psi_{a,3}$ 20.7 | Between outer & inner rings | 0.063 | n/a |
| $\psi_{a,4}$ 24.1 | Acoustic core: outer+inner | 0.057 | 0.25 |
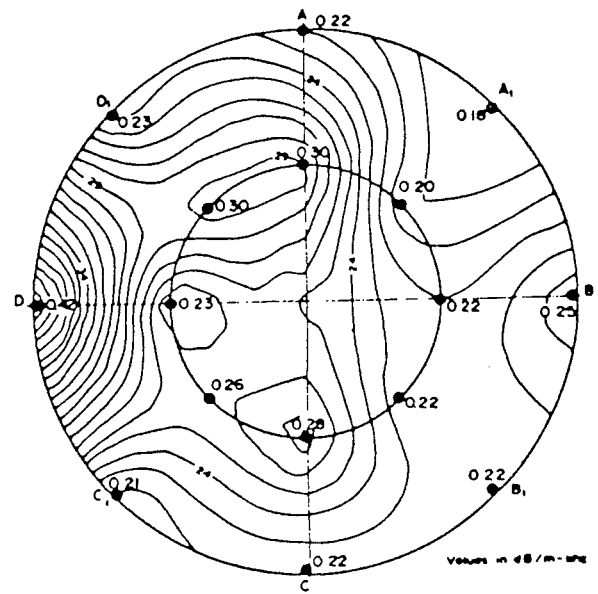
FIG. 6d    Attenuation Isolines

ACOUSTIC SUB-SURFACE INTERROGATOR

This invention relates to a method and apparatus for investigating physical properties of structures.

One area of application for this invention is in the investigation of the structure lithology of the seabed.

The identification of possible sub-seabed hazards is important to the safety and economics of offshore hydrocarbon drilling and development programs. Hazards in the upper tens of meters can include boulders, hydrate and gas accumulations, permafrost and exceptionally soft sediments. Knowledge of such hazards enables safe drilling and casing procedures to be established in the early phases of a program. Detection of these same hazards is important in the siting of bottom founded offshore structures, such as jack-up rigs and gravity based production platforms.

The conventional means of detecting shallow, sub-bottom hazards are high resolution seismic profiling, supplemented by actual coring of the sediments. The seismic data are normally collected using a sound source and hydrophone array towed behind a vessel and the reflections from the different geolocial horizons are displayed as a continuous "vertical strip" along the track of the ship. However, such systems do not have the spatial and temporal resolution required to distinguish the presence of boulders and cobbles, or to identify the infill material in buried river channels. When detailed knowledge of a specific site is required, such as for a jack-up drilling operation, actual cores of the seabed have to be obtained for measurement of geotechnical properties prior to regulatory approval.

It is frequently found that there is little or no apparent correlation between the visible layering in the seabed core and the acoustic horizons mapped using the seismic equipment. These inadequacies in the current technology have resulted in the failure to identify hazards and multi-million dollar costs due to the consequent disruption of drilling operations.

Consequently, there is a need for an acoustic device which accurately identifies the physical properties of structures.

According to the invention, there is provided a method for investigating sub-surface acoustical properties of a layered site, comprising the steps of selecting a plurality of primary scanning locations at a site, generating at least one sonic pulse for calculating the speed of sound in water at said scanning locations, for each scanning location, undertaking at least once the sub-steps of selecting a power, resultant centre frequency, beamwidth, bandwidth, shape and incident angle for an input signal, said incident angle chosen so that a significant portion of the energy in the input signal will enter the site, insonifying said scanning location with said input signal, receiving reflected signals; and predicting subsurface acoustical properties of layers of said site at said scanning location from said reflected signals and said at least one sonic pulse.

According to another aspect of the invention there is provided apparatus for determining sub-surface acoustical properties at a layered site comprising: a stationary platform; transducer means moveably supported by said platform for insonifying scanning locations at said layered site with a signal of variable power, shape, bandwidth, centre frequency, beamwidth and incident angle; receiver means moveably supported by said platform for receiving signals reflected from said layered site; and processor means for determining acoustical properties of layers of said site at said scanning locations from the characteristics of said insonifying signals and said reflected signals.

At present, subseabed sampling and in situ measurements of soil parameters determine the properties of a soil at a single location and measure the variability of that soil with depth at that location. A vertical profile of information is obtained. The detail with which the soil can be described along the length of the borehole is dependent on the interval of sampling. Extrapolation of properties across a horizontal plane is generally done through correlation with measurements at adjacent boreholes. Complementing this are seismic methods or techniques which effectively map two-dimensional profiles within a vertical plane between the measurement locations.

If reliability estimates, computer aided spatial integration, and topographic representation of soil property distribution are to be attempted, then three-dimensional images of soil properties are required.

The present invention allows three-dimensional mapping of geophysical parameters of the subsurface with much greater accuracy than is currently attainable using conventional seismic site surveying procedures.

In the figures which represent example embodiments of this invention:

FIGS. 6a through 6d show an example of a typical acoustic core product.

Figure 1:
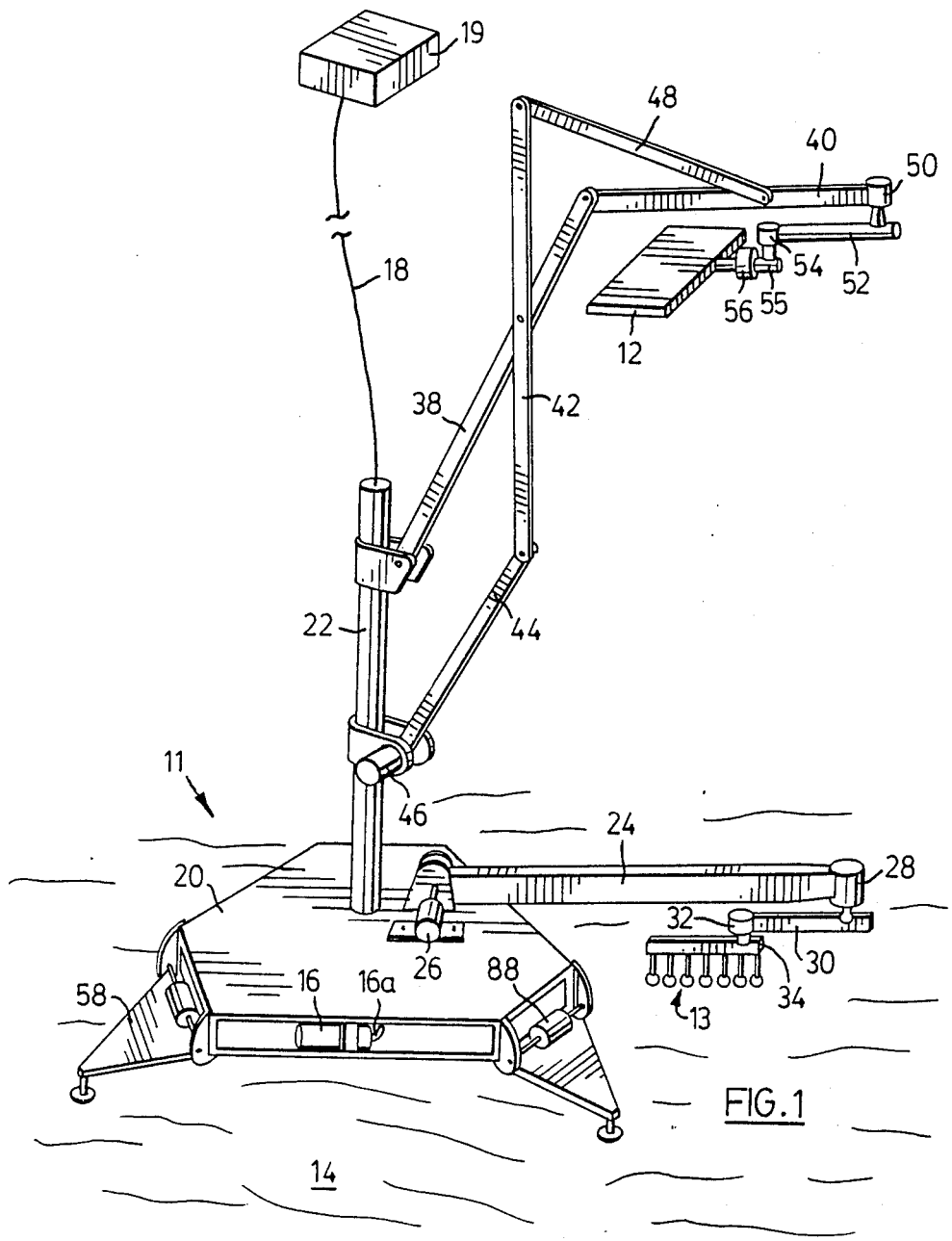
FIG. 1 is a perspective view of an acoustic subsurface interrogator made in accordance with this invention.

To accurately represent true subsurface geology using acoustics it is paramount that the temporal resolution be sufficiently high to prevent interference within the layers. This essentially means an infinitively sharp change in amplitude such as in a step function. In the time domain this would require an infinitely short pulse.

It is not always feasible however to have such a short pulse using conventional acoustical sources (eg. transducers). The length of the outgoing signal is a function of the pulse bandwidth. The pulse bandwidth determines the sharpness of the amplitude change with frequency near resonance or Q of the system. As the bandwidth is increased, the pulse length will shorten and the Q of the system will lower. Unfortunately a decrease in Signal-to-Noise power ratio will also occur proportionally to the shortening of the pulse length; efficiency being a function of Q. An increase in bandwidth will also engender an increase in ambient noise. Since the absorption loss in a sedimentary structure is dependent on frequency, a decrease in Signal-to-Noise is a serious constraint on the frequencies available in the propogation.

If the nature of the sedimentary structure is considered seismically hard whereby its composition includes angular particle shapes, rather high grain size distribution and variable porosity, the resultant attenuation at high frequencies will be large. The acoustic sources used in the subject acoustic subsurface interrogator should have a broad bandwidth transient signal and a high Signal-to-Noise Ratio, since otherwise the resulting resolution and penetration potential will be limited. With the advent of non-linear acoustics (i.e. parametric arrays), high resolution sources can be created which are capable of meeting very high levels of temporal and spatial resolutions. Therefore the use of parametric arrays in the subject acoustic sub-surface interrogator is preferred. A significant advantage of such a source is that its signal shape can be tailored easily, a property which can greatly enhance subsurface layer identification and aid in making the attenuation measurements. The main attributes of applying non-linear acoustic techniques for the invention are that:

(i) a narrow beamwidth at a low frequency can be obtained,
(ii) the low frequency used can be varied over a wide range with ease and simplicity, and
(iii) wide bandwidth signals can be used and varied in order to obtain high temporal resolutions.

Parametric arrays are conventionally generated through a process called "self-demodulation". If a modulated carrier frequency signal is radiated from the acoustic transducer, nonlinear interaction takes place in the water between all the frequency components present by virtue of the modulation envelope. The secondary signal thus produced in the water contains a band of difference frequencies and has a time domain form proportional to the second time derivatives of the square of the modulation envelope.

Unfortunately, these attractive virtues of a wide bandwidth and narrow beamwidth are bought at the cost of low power efficiency and with a stringent requirement for a very stable transmission path. In the present invention it has been recognized that the effect of these limitations may be minimized by providing a transmitter and receiver fixed at a given spot over, and proximate, the seabed. The precise height the acoustic sources can be maintained at, above the seabed to maximize the application of a parametric array is discussed hereinafter. The parametric source volume is intentionally truncated in the region of the transmitting transducer nearfield - farfield boundary coinciding with the water/sand interface. The seabed surface causes the termination. This essentially provides for an optimized shock distance to coincide with the entry of the signal into the seabed; thereby maximizing the efficiency of the source.

By way of overview, referring to FIG. 1, the acoustic subsurface interrogator is indicated generally at 10 and comprises a stationary platform 11 for precisely positioning transducer means 12 and an array of hydrophones 13 above the seabed 14. Cannister 16 houses instrumentation and electronics for the platform. The device 10 is tethered to a ship by an umbilical cord 18 through which data is transmitted between the device and a shipboard computer 19. In operation, the transducer means is used to generate a signal with a desired resultant centre frequency, bandwidth, shape, beamwidth, power and angle of incidence.

The device begins by sounding the seabed, then deeper reflectors in the sediment column are identified by a digital signal analysis algorithm. In a methodical sequence, the device incorporates the sonic velocity of the water layer with multi-offset soundings of the next deeper reflector to determine its fidelity as a primary reflector, and, using well understood seismic theory, to deduce velocity in that layer from arrival time versus incident angle information. Attenuation is quantified by analysing the return signal once the velocity of the layer is known. Then, using the acoustic properties and thickness of the first layer, the device can carry on to deeper reflectors. Signal-to-noise ratios can be boosted at greater depths by invoking greater signal averaging, or penetration can be enhanced in trade for resolution at great depth by varying the centre frequency. The device is able to adapt in response to the observations being made. Calibrated changes in the signal bandwidth and wave shape are easily manipulated during the interrogations.

Figure 6A:
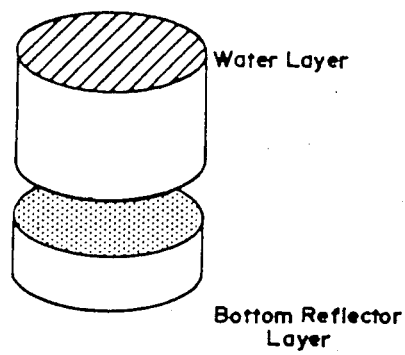
Figure 6B:
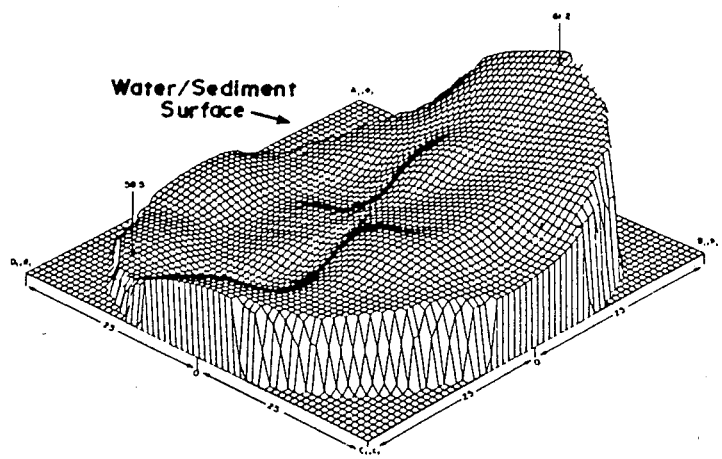

The results can be presented graphically as an "Acoustic Core" as illustrated in FIG. 6. Even though no drilling takes place, a characterization of the sub-seabed sediment properties "grows" downward as the operator onboard ship monitors the device's progress. At a given "Acoustic Core" site several locations lying on concentric circles (referred to as a Spatial Offset Network) may be acoustically sampled in order to provide a statistical sample over which averages are taken, and to quantify the inhomogeneity of the layer being insonified. This is especially pertinent to the detection and characterization of bouldery layers.

Returning to FIG. 1, a more detailed discussion follows. Base 20 of platform 11 supports rigid mast 22 and boom 24. Motor 26 controls the elevation of boom 24. Boom 24 terminates in motor 28, the rotor of which is connected to swivel arm 30. Swivel arm 30 terminates at motor 32, the rotor of which is connected to swivel arm 34. Swivel arm 34 supports mounting fingers 36. The mounting fingers support the hydrophones 13.

Scissor arm 38 is pinned at one end to mast 22, at its other end to boom 40, and medially to scissor arm 42. Connecting rod 44 is mounted at one end to the rotor of mast mounted motor 46 and is pinned at its other end to one end of scissor arm 42. A connecting rod 48 is pinned at one end to the other end of scissor arm 42 and at its other end to a medial portion of boom 40. The free end of boom 40 terminates in motor 50, the rotor of which is connected to one end of swivel arm 52. Swivel arm 52 terminates in motor 54, the rotor of which is connected to swivel arm 55. Swivel arm 55 terminates in two-axis drive 56. Two-axis drive 56 supports the transducer means 12.

Legs 58 are pivotally connected to the base 20 of platform 11. Motors (not shown) control the angle the legs make with base 20. The mast, booms, arms and connectors are hollow tubes. Electrical lines 16a run within the hollow tubes between the cannister 16 and the hydrophones, the transducer means and the various motors. Umbilical cord 18 also feeds into the cannister 16.

Before the platform is lowered to the seabed, booms 24 and 40 and legs 58 are pivoted to a vertical position. This assists in protecting the transducer means and the hydrophones from damage during descent. As the platform reaches the bottom, legs 58 are deployed to level and stabilize the platform. Level indicators in cannister 16 assist in this regard. If the platform is able to attain a horizontal position within a pre-set tolerance, and if the current, as measured by current sensors (not shown), is within tolerance, then the booms 24 and 40 are deployed. In this regard, motors 26 and 46 are used to move booms 24 and 40 (respectively) to the horizontal with a high degree of accuracy.

It will be noted that, after deployment, the transducer means may be made to describe a circle by actuating motor 50. The radius of this circle may be varied by varying the angle between swivel arm 55 and swivel arm 52 by means of motor 54.

In a similar manner, hydrophones 13 may be made to describe a circle of selectable radius. Two-way drive 56 allows the transducer means to be inclined from the horizontal.

For reasons set out hereafter, the device of FIG. 1 is scaled so that the transducer means may be held 8.5 m off the seabed. The hydrophones 13 are held about 1 m above the seabed in order to ensure they do not come in contact with the bottom.

The transducer means 12 may be any known transducer or transducer array suitable for undersea environments which can produce stable, reproducible, coherent signals. A parametric array is preferred and hereinafter the transducer means 12 will be referred to as a transducer array. The crystals are operated by crystal electronics detailed in FIG. 2. A carrier frequency generator 120 produces a carrier frequency which is modulated in a double balanced mixer 124 by a haversine pulse produced by pulse generator 122. Generators 120 and 122 are under the control of controller/processor 140. The resultant amplitude modulated carrier is fed to a linear amplifier 126 and hence to transformers 128 matched to each crystal 70. The transformer output signal excites each crystal to produce a Gaussian modulated acoustic pulse 130. As is well known, when a Gaussian modulated acoustic pulse 130 travels through a non-linear medium, such as water, it self demodulates to form a Ricker wavelet 132. For a Gaussian modulated carrier, the process produces a Ricker wavelet of similar time duration to that of the carrier pulse and with a bandwidth determined by the modulating pulse and the carrier frequency.

By selecting the period and amplitude of the carrier and the haversine pulse, the resultant centre frequency, power, bandwidth, beamwidth, and shape of the Ricker wavelet may be controlled. The transducer array 12 thus operates as a parametric array. Two-way drive 56 of FIG. 1 allows the selection of the direction (angle of incidence) of the acoustic beam.

It should be noted that there are other known means to generate a non-linear signal from the transducer array. For example, the crystals may be energized with two slightly different high frequencies. The interaction of the two beams in the water column then produces a non-linear wavelet at a secondary difference frequency.

The optimum total area of the transducer crystals and the target height above the seabed assuming the transducer array is being operated in a parametric array mode may be derived from the following.

The difference frequency pressure in the frequency domain (P(wd)) as a function of range (R) and angle of incidence ($x_1$) for the far field (i.e. the range at which the acoustic pulse has self demodulated) may be obtained from the following equation which is known to those skilled in the art:

$$P(\omega) = P_o^2 \omega d^2 2 \sqrt{2\pi} \frac{a^2 l}{R} \cdot \frac{J_1(x_1)}{x_1} \cdot \frac{\sin(x_2)}{x_2} \cdot \frac{\beta}{8\pi\rho c^4}$$

where:
  $P_o$ is the power input to the array in Watts,
  $W_d$ is the difference frequency of the signal in the farfield in rads (i.e. $w_d$ is the difference between the upper and lower 3 dB frequencies of the signal),
  a is the radius of a circular array in m,
  l is source height above the seabed in m,
  c is the speed of sound in the surrounding medium, or 1500 m/s for water,
  $x_2$ is the angle of reflection, in rads,
  $\beta$ is a constant of value 3.5 for water, and
  $\rho$ is the density of the medium, or 1000 kg/m³ for water The on-axis far field pressure, reduced to a unit distance (R=1) is $$P(\omega,1) = \frac{P_o^2 \omega d^2 2 \sqrt{2\pi} \, a^2 l \beta}{8\pi\rho c^4} \tag{1}$$

If we let the power radiated $W = \frac{P_o^2 a^2 \pi}{2\rho c}$ then $$P(\omega,1) = \frac{W\omega d^2 l \beta}{c^3 \pi \sqrt{2\pi}}$$

The Source Level of the difference frequency in the farfield will be 20 log (P(w,1) or SLd. Therefore:

$$SL_d = 144.88 - 60 \log c + 40 \log f_d + 20 \log W = 20 \log l \tag{2}$$

where $f_d = wd/2\pi$ in $H_z$.

The power radiated, the transducer radius and the carrier frequency (fc) will have to be optimized in relation to l in order to attain a maximum Source Level. This means that the shock distance must be greater than or equal to the range to the termination of the parametric array (the seabed) and to the carrier nearfield. For instance, shock is said to have formed at a range:

$$R_s = \frac{\rho c^2}{k_c P \beta}$$

(or $(k\epsilon\beta)^{-1}$) which can be defined as the Acoustic Mach Number with $$\epsilon = \frac{p}{\rho c^2}, \, k = \frac{2\pi f_c}{c}$$

with $f_c$ being the primary carrier frequency.

From (1) $P^2 = \frac{2\rho c W}{\pi a^2}$ with $\frac{W}{\pi a^2} <$ $10^4$ watts/m² then $p^2 < 2\rho c \cdot 10^4$.

Therefore, taking the equalities $$l = R_s = \frac{\rho c^3}{2\pi f_c \beta \sqrt{2\rho c} \cdot 10^2}$$

which finally reduces to $$l = \frac{c^2 \sqrt{\rho c} \cdot 10^{-2}}{2\sqrt{2} \, \pi f_c \beta}$$

Assessing the carrier frequency in terms of l derives:

$$f_c = \frac{c^2 10^{-2}}{2\pi\beta l} \sqrt{\frac{\rho c}{2}} = \frac{885918}{l} \text{ (in hertz)} \quad (3)$$

The radius a of the transducer can be established in terms of l, when $1 \leq$ the carrier nearfield, $$a > \sqrt{l\lambda_c} \text{ or } \sqrt{\frac{lc}{f_c}} \quad (4)$$

Finally, evaluating W in terms of l, given that $W = \pi a^2 \cdot 10^4$ watts, defines W as $$W = \frac{\pi l c 10^4}{\frac{886 \cdot 10^3}{l}} = \frac{\pi l^2 c 10^4}{886 \cdot 10^3} = 53.19 \, l^2 \quad (5)$$

Thus the maximum Source Level at the difference frequency ($f_d$) in the farfield of the terminated Parametric Array will become:

$$P(\omega,1) = \frac{W 4\pi^2 f_d^2 l \beta}{\sqrt[3]{2\pi}} = 2.765 \cdot 10^{-7} f_d^2 l^3$$

or
$$P(\omega,1) = l^3 f_d^2 \cdot 2.765 \cdot 10^{-7}$$

Rewritting $P(\omega,1)$ as $SL_d$ the Source Level then can be expressed in dB re 1 $\mu$Pa:

$$SL_d = -11.17 + 60 \log l + 40 \log f_d$$

The radius, the carrier frequency and the power for the terminated Parametric Transducer as a function of height above the seabed are noted as optimum levels when expressions (3), (4) and (5) are in accordance. A height l of greater than 10 meters above the seabed is considered to be a very real practical engineering limit to the stable in-situ positioning of sonar transmitters. Therefore the 10 meter height has been set as a design boundary. A minimum carrier frequency $f_c$ of around 100 kHz establishes a second criteria since the difference frequency $f_d$ can inherit the bandwidth of the source at the carrier frequency. For instance, a carrier frequency much lower than 100 kHz at a particular Q would tend to provide a bandwidth on the low side (i.e. $\Delta f = f/Q$). As well, the reduced attenuation associated with a lower carrier frequency may make the discrimination of the carrier from the resulting difference frequencies received from the upper layer of the seabed, difficult.

An optimum Source Level can therefore be obtained as the source height approaches 10 meters and does not significantly exceed the lower $f_c$ boundary of about 100 kHz. On this basis, a carrier frequency of 95 kHz was selected. This designated an optimum height of 8.5 meters and a circular transducer radius of 0.38 meters, yielding a transducer area of 1.2 m². The matching power output is 3,483 watts.

The array of hydrophones 13 may comprise any known strongly directional array, such as a linear array of a plurality of omnidirectional hydrophones.

Figure 2:
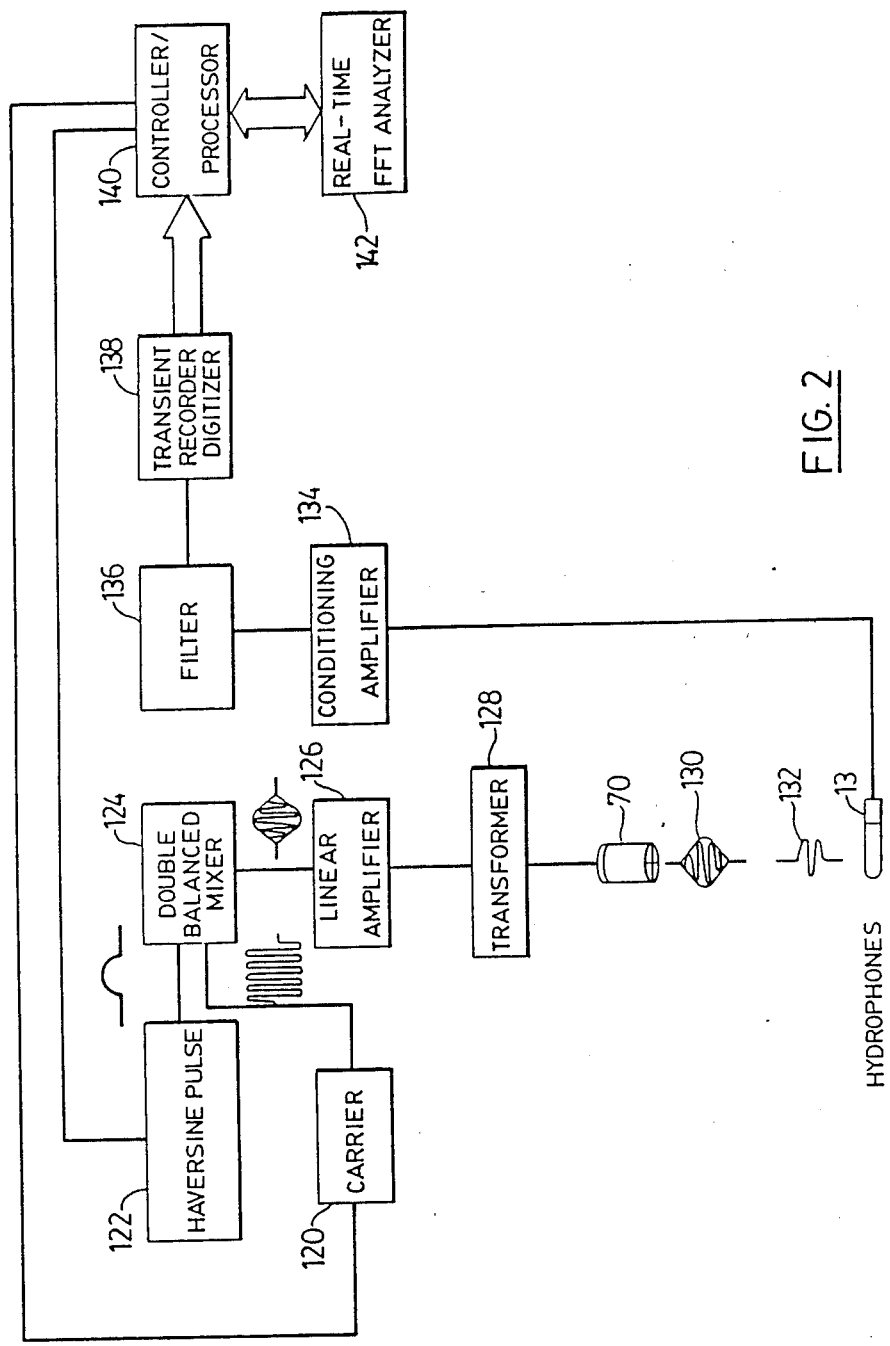
FIG. 2 is a schematic view of a portion of the electronics for the device of FIG. 1.

Suitable hydrophones are model 8105 hydrophones manufactured by Bruel & Kjaer. The electronics for the hydrophones are shown in FIG. 2. Returning signals pass through a conditioning amplifier 134 and a filter 136. The filter is a band-pass filter to eliminate noise. The analogue signals are next digitized by the transient recorder digitizer 138 and then processed by the controller/processor 140 and real-time FFT analyser 142, as is described more fully in connection with FIGS. 3a and 3b.

Figure 3A:
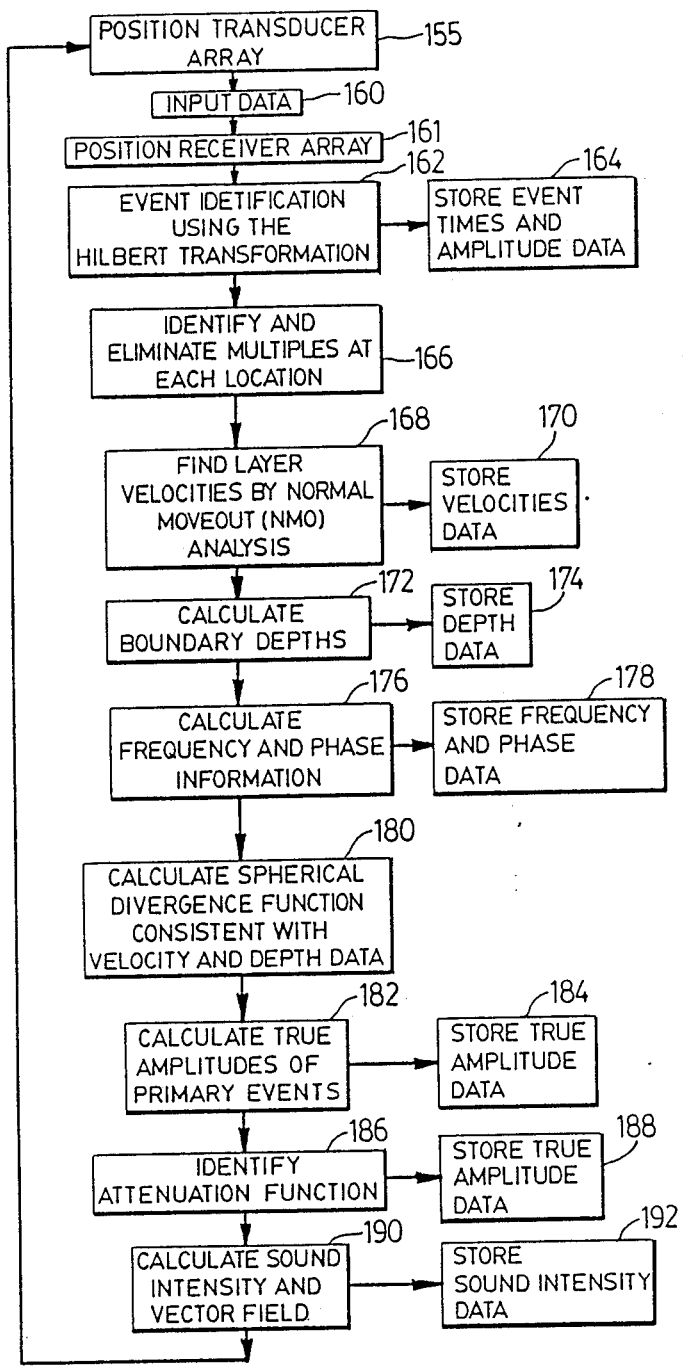
FIGS. 3a and 3b are flow diagrams of the logic for the operation of the device of FIG. 1.

The manner of use of the device after it is deployed on the seabed at the site to be scanned is described in connection with FIGS. 3a and 3b. The steps of FIG. 3a are taken by controller/processor 140. The transducer array is positioned over a location within the site and is tilted to selected incident angles (box 155). A series of amplitude modulated input pulses are then fed to the transducer array so that acoustic inverse Ricker wavelets of desired resultant centre frequency, bandwidth, beamwidth, shape, power and incident angle insonify on the seabed (box 160). After the first location has been fully interrogated (via the steps of boxes 162 to 192 of FIG. 3a, which are described more fully hereinafter), the transducer is then moved to the next location at the site and the interrogation process repeated. The device is used to interrogate locations at the site which lie on a notional inner scanning ring and a concentric notional outer scanning ring, as shown in FIG. 4. Each ring has eight primary scanning locations "A" through "D1" and "a" through "d1" equally spaced about the circumference of the ring and arranged such that a radial line from the common centre which intersects a scanning location on the inner ring will also intersect a scanning location on the outer ring.

An outer and an inner concentric scanning ring are employed in order to create a statistical base to quantify the homogeneity of the layer along each scanning circumference and the homogeneity along a radial path between the inner circle and the outer circle. The inner circle acts as a statistical origin.

While it would be possible to scan a site with a different scanning pattern, concentric rings allow for equal distances between the primary scanning locations around each ring and for the radial distances between the rings to be constant. Maintaining uniform distances simplifies the statistics necessary to obtain useful results.

The outer ring has a maximum diameter of 5 m and the inner ring has a minimum diameter of 1 m. These dimensions allow for the statistical determination of two meter size boulders as well as the clay/silt distribution of a sediment matrix.

Waves propogating into a seabed may encounter variations in the sedimentary composition of the medium. If a significantly different gradient occurs, a reversal of the waves propogation will result with a portion of the energy returning to the surface. Along with the arrival of this primary reflection, other energy will also follow in the form diffraction, reflected refraction and multiple reflections.

A particular input pulse (at a given location on a scanning ring) is repeated and the receiving array moved until all return signals are captured (box 161). The returning real-valued time domain signals are mapped by the Hilbert transform to analytic signals of the form $z(t) = E(t) \exp(j\theta(t))$ where $E(t)$ is the envelope signal and $\theta(t)$ is the instantaneous phase signal (box 162) and stored for analysis (box 164). The peaks in the envelope signal correspond to the reflection interfaces.

Figure 5:
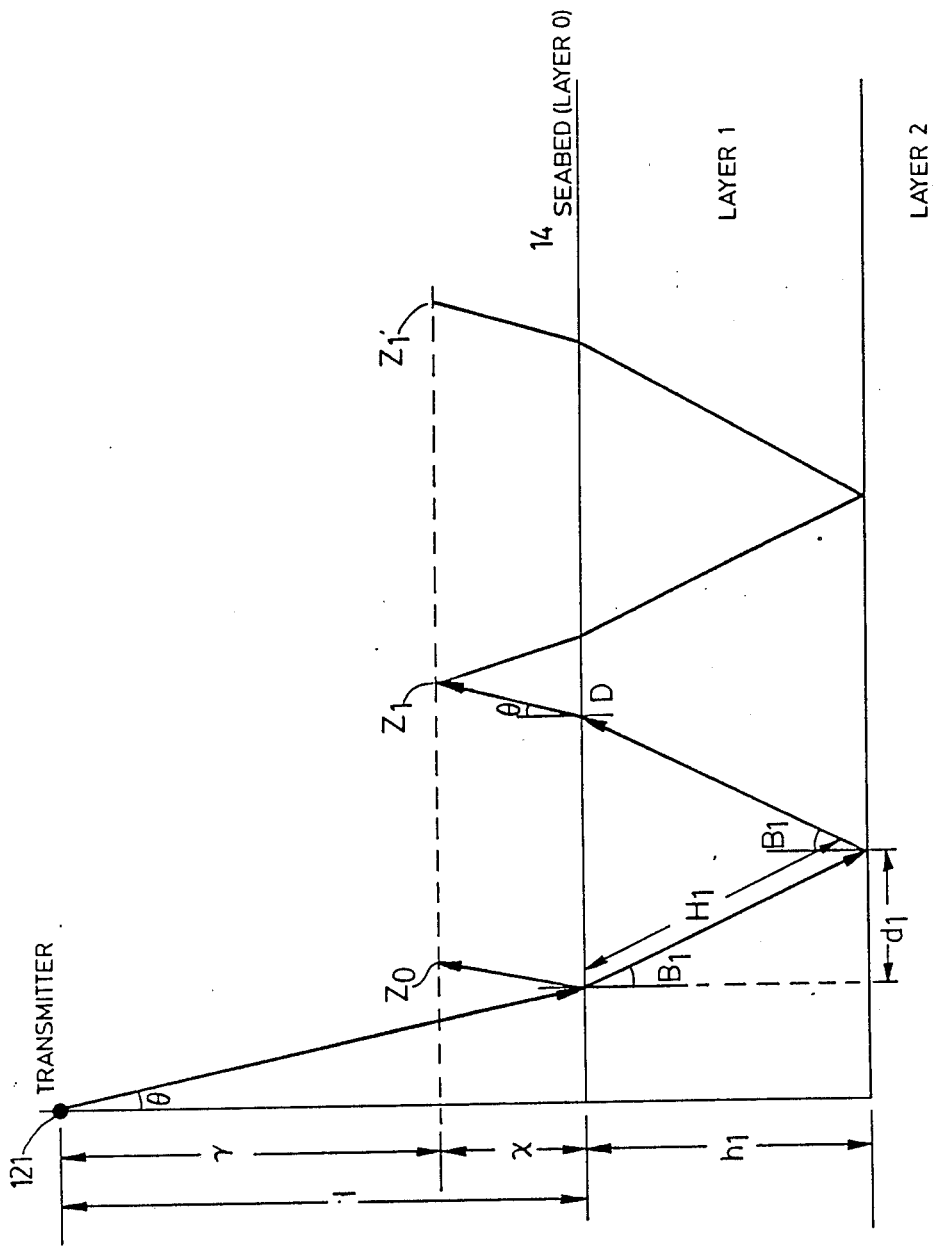
FIG. 5 is a ray diagram showing portions of the path of an input pulse.

FIG. 5 is a schematic representation of the transmission and reception geometry, wherein the transducer array is illustrated schematically at 121 and wherein:

- $l$ is the height of the transducer array above the seabed;
- $\chi$ is the height of the hydrophone array above the seabed;
- $h_1$ is the thickness of the first sub-seabed layer, layer 1.

The incident and reflection angles have been exaggerated for clarity of the schematic. True echos may be distinguished from multiples as follows. The arrival time (T) and position (z) of the seabed return are captured. The next echo that could follow the seabed reflection is a signal coming off the first sub-seabed layer. This can be easily corroborated. Thus, $Z_1$ can be measured.

Using the information corresponding to the seabed echo and to the first layer reflection, the first order multiple off Layer 1 is then predicted for a selected transmission angle 0. For instance, by applying the seabed echo's time of arrival and its position z the following computations develop:

$$z_o = l \tan(\theta)$$

This will set for Layer 1

$$d_1 = (z_1 - z_o)/2$$

The travel time of the first order multiple ($t'_1(0)$) reflected within the upper and lower boundaries of Layer 1 is expressed in terms of a two-way travel (slant) time ($t'_1(0)$) of the primary echo from Layer 1.

$$t'_1(\theta) = 2 t_1(\theta)$$

Likewise, the total time ($T'_1$) is written to include the travel time from the transmitter into the layer plus the time for a multiple reflection to take place in addition to the departure time out of the layer until the signal is captured at a position z.

$$T'_1(\theta) = T_1(\theta) + (t'_1(\theta)/2)$$
$$= T_1(\theta) + t_1(\theta)$$

Finally, the position z is predicted for the first layer multiple by applying $$z'_1 = z_1 + 2d_1 = 2z_1 - z_o.$$

The received signal following the Layer 1 echo return is correlated with the predicted multiple path time $T'_1(\theta)$ and position $z'_1$ assuming a flat layer with no dip and for small offset $z'_1$ - assumptions which normally hold for sub-seabed soil. If the echo time and position correspond, the return signal is identified as the multipath return associated with Layer 1. If they do not accord within an established error range, then the signal is interpreted to belong to a true primary reflection coming off Layer 2. Hence the Layer 2 primary echo is identified. Following this, the predictive iterations are applied again for the multiples that might result within the physical confines of Layer 2. A correlation is made with the actual reflection arrival times and positions. An identification of either a true echo or of a multiple results. The procedure is then repeated for the next set of signals.

The position and time for multiples of any layer n can be found by employing:

$$T_n(\theta) = T_n(\theta) + t_n(\theta)$$

and $$z'_n = z_n + 2d_n = 2z_n - z_{n-1}$$

given that $d_n = (z_n - z_{n-1})/2$ (box 166).

The speed of sound in water $C_o$ may be found by generating a sonic pulse at normal incidence from the transducer array to the hydrophone array and realising $C_o = \gamma/t$ where $\gamma$ is the distance between the transducer array and the hydrophone array in the normal incidence position and t is the transmission of the direct arrival of signal transmission. Depending on the quality of the water, it may be desirable to determine $C_o$ for each position on a scanning ring or merely once for the entire scanning site.

A measurement of the acoustical property of the velocity of propogation of sound can now be attempted for each layer (at a set transducer position) given that their z position and time are known. Snell's Law is applied to account for the raypath bending that a propagation will encounter in passing through different velocities. Using the transmission angle $\theta$, the resultant propagation angle $\beta$ can be obtained from:

$$\frac{\sin\theta}{c_o} = \frac{\sin\beta}{c_1}$$

where B and c, are, at this point, both unknown; and for all cases that follow:

$$\frac{\sin(\beta_n)}{c_n} = \frac{\sin(\beta_{n-1})}{c_{n-1}} \tag{6}$$

where $\beta_o = \theta$. By rewriting expression (6), $c_n$ is defined as $$c_n = \frac{c_{n-1} \sin(\beta_n)}{\sin(\beta_{n-1})}$$

Since $\sin(\beta_n) = d_n/H_n$ then $c_n$ can be stated as $$c_n = \frac{c_{n-1} d_n}{H_n \sin(\beta_{n-1})} \tag{7}$$

where $H_n$ refers to the slant height of the ray path in the $n^{th}$ layer which is unknown at this stage. Likewise, $c_n$ can also be denoted by $$c_n = \frac{2H_n}{t_n(\theta)} \tag{8}$$

Combining expressions (7 and 8) enacts this relationship:

$$\frac{c_{n-1} d_n}{H_n \sin(\beta_{n-1})} = \frac{2H_n}{t_n(\theta)}$$

Since
6
$$H_n^2 = h_n^2 + d_n^2$$

$h_n$ can be written as $$h_n = \sqrt{\frac{c_{n-1}d_n t_n(\theta)}{2\sin(\beta_{n-1})} - d_n^2}$$

It therefore follows that $$c_n = \frac{2\left(\sqrt{\frac{c_{n-1}d_n t_n(\theta)}{2\sin(\beta_{n-1})} - d_n^2}\right)}{t_n(0)}$$

where $t_n(0)$ is equal to the normal incident arrival time and/or to $$\frac{h_n t_n(\theta)}{\sqrt{h_n^2 + d_n^2}},$$

$c_o$ is the velocity of water, $\beta_o$ is the transmission angle and $d_n$ is equal to $(z_n - z_{n-1})/2$. Note that $t_n(\theta)$, $d_n$ and $\beta_o$ through $\beta_{n-1}$ must be calculated each time for each successive layer.

This procedure for determining h and c requires iterations that start at the first layer and then follow in a sequential manner.

The iterative procedure to calculate velocity and boundary depths are shown at boxes 168 and 172. The results of these calculations are stored (boxes 170 and 174, respectively).

A fourier transform is applied to the primary reflections from each layer (box 176) and the frequency and phase information is stored (box 178).

An indication of the spherical divergence from the velocity and depth calculations is then derived (box 180).

The next phase in the interrogation involves the characterization of the attenuation loss distribution. This is accomplished through the use of the power spectrum stored as the result of box 178. The frequency corresponding to the peak pressure level of the returned signal from the water/seabed interface establishes a reference frequency $f_{max}$. The corresponding spectral level pressure at this frequency is recorded (boxes 182, 184) and used as a reference pressure. The spectral level at the reference frequency is read from the spectrum of the echo belonging to the layer 1/layer 2 interface (boxes 182, 184). The difference between the reference reading and the layer 1/layer 2 interface value derives the attenuation loss for the layer (boxes 186 and 188). This may be repeated for subsequent layers since the energy of the propagating signal is known at the onset and accounted for as it gets redistributed in the form of reflectioning backscatter and attenuation from one layer to the next.

The attenuation loss can be rewritten into an absorption coefficient after considering the thickness of the layer at the specific scanning position and after accounting for the reference frequency used in making the measurements.

The sound intensity and vector field are next calculated and stored. (Boxes 190 and 192).

The steps of boxes 160 to 192 were described in connection with input pulses at a single scanning location. To generate the data described hereinbefore, pulses are required at each scanning location at a small non-zero degree angle with the vertical. (A large angle with the vertical would result in most or all of the energy in the signal being reflected at the seabed.) An angle of 3° with the vertical has been found to be a convenient choice. As will be described in connection with FIG. 3b, additional pulses may be generated at a particular scanning location (having different parameters) if the return signals from the initial pulses are too severely attenuated or non-existent. The hydrophone array is repositioned while the transducer array generates repetitive pulses until a full set of data regarding the return signals is generated. While the speed of sound in water could be calculated from these pulses, a normal incidence pulse is convenient for this calculation since the vertical distance between the transducer array and hydrophone array is known.

The steps of boxes 160 to 192 are repeated under control of the controller/processor 140 for subsequent scanning locations (return line to box 155) at the site so that each of the scanning locations described in connection with FIG. 6 are interrogated.

Figure 3B:
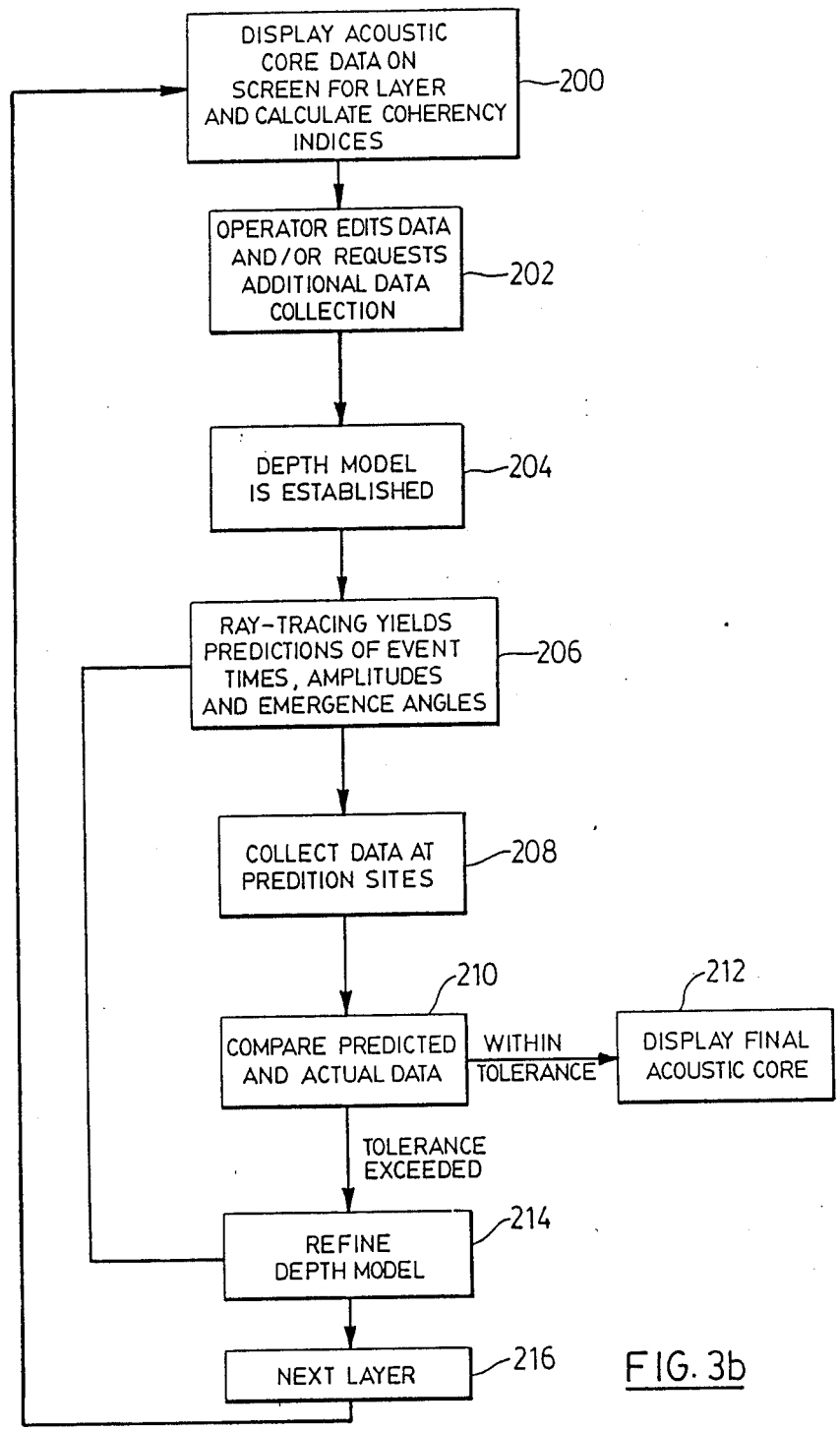
Figure 4:
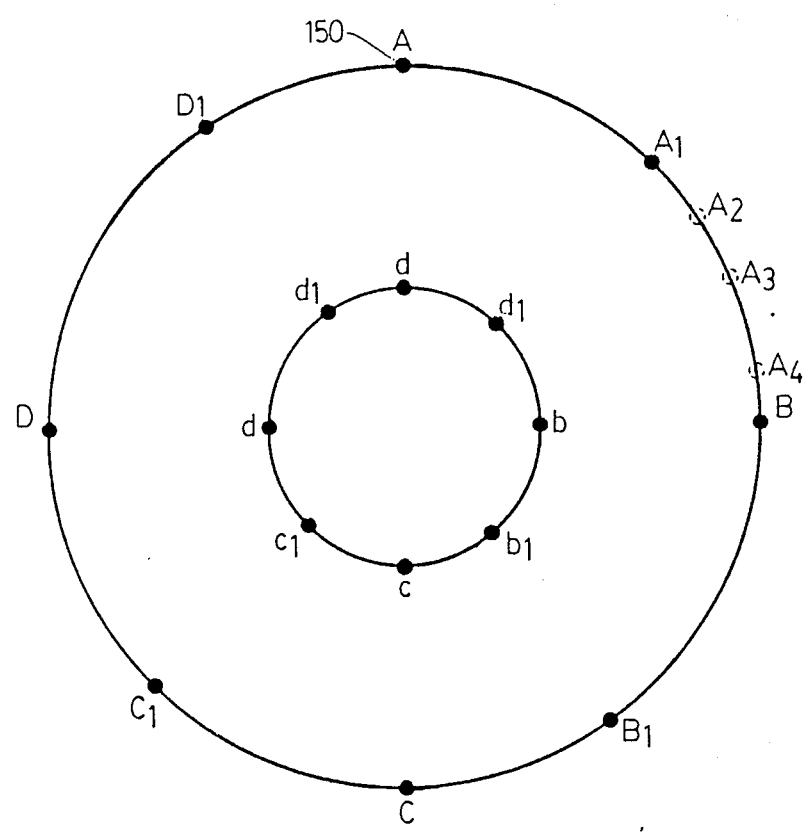
FIG. 4 is a schematic view of scanning locations at a site.

The procedure of FIG. 3a executed by controller/processor 140 of FIG. 2 is under the control of an operator and/or supervisory system undertaking the procedure of FIG. 3b.

Turning to FIG. 5b, the data of the first layer is displayed as it is collected (box 200).

To provide an evaluation of variance in the first layer between measurement points, the standard deviation (S) is employed. A coherency scale ($\psi$) is developed which incorporates the standard variance:

$$\psi = 100 e^{-rx}$$

where r defines the slope or sensitivity of the coherency scale and x is the normalized deviation defined as follows:

$$x = S/\bar{S}$$

$\bar{S}$ is a constant which represents the maximum deviation of the acoustical parameter (velocity or attenuation) being evaluated. Since deviation S within the scanning rings is expected to be low, the scale accentuates the deviation nonlinearly to produce greater sensitivity for the low S data. The maximum coherency ($\psi = 100\%$) occurs when S=0, indicating that the parameter being compared is totally coherent between the different positions.

(a) Coherency Scale for Velocity ($\psi_c$)

To derive the coherency scale for velocity, the constant $\bar{S}$ is equated to a maximum velocity deviation for the propagation medium. It is known that the velocity range for subseabed sediment is from 1500 to 2500 m/s. Therefore the value of $\bar{S}$ for sediments can be set at 1000 as a first estimate. This yields an expression for the velocity coherence scale as $$\psi_c = 100 \, e^{-rs/1000}$$

The value of r is subjectively set in context to the sensitivity required for the scale. For example, for a glacial till, $\psi_c$ is low. Therefore a value of 50 may be assigned to the sensitivity factor (r). Its value can be adjusted to accentuate data trends.

(b) Coherency Scale for Attenuation ($\psi_a$)

The value of S in the attenuation coherency scale is set to a maximum attenuation coefficient deviation for the medium of propagation. For sediments, the attenuation coefficient values is known to vary between 0 and 1 dB/m-kHz. Therefore, $\bar{S}$ is set to 1, thus defining the attenuation coherency scale as $$\psi_a = 100 \, e^{-rs}$$

The value of r may be set at 25. As in the case of the velocity coherency scale, the sensitivity factor can be adjusted.

(c) Coherency Indices

The scales developed for velocity and attenuation formulate coherency indices for a layer which allow:
(i) comparisons along the scanning circumferences (outer and inner),
(ii) comparisons along a radial path between the inner circle and the outer circle,
(iii) treatment of the outer and inner scanning circumferences together. (box 200)

If a coherency indice shows a low coherency (and hence a significant change in a property) between the primary scanning locations, additional secondary locations are chosen between the primary scanning locations as necessary to fully document the change. For example, if the coherency in a property between A1 and B on the outer scanning ring falls below an operator preset bound, additional secondary scanning locations A2 to An are interrogated on the outer scanning ring between locations A1 and B as necessary until the changing property is fully documented (box 202). The operator may also request additional interrogations with different parameters if the return signals are too severely attenuated.

The data developed from the discrete scanning locations are then used to develop a continuous depth model of the first layer at site (called an acoustic core) refer to FIG. 6. As well, the frequency pattern along with the time domain magnitude can codify composite reflections into indicators of a complex lithology. Certain sedimentological conditions would alter the change in Instantaneous Frequency more readily or dynamically than what would normally be observed (box 204).

Based on the model for the layer, the return signals for a new scanning location or a different parameter pulse are predicted (box 206) and data is collected at the prediction sites (box 208). If the actual and predicted data compare favourably (box 210), the model of the layer is verified and may be displayed (box 212). If, however, the predicted and actual data do not compare within a pre-selected tolerance, the model is refined based on the further actual data (box 214) and further predictions and attempts at verification are conducted (boxes 206 to 214) until the model is verified.

The next layer is then selected (box 216) and the process repeated from box 200, so that the acoustic core grows downwardly.

An acoustic core model for larger sites may be developed by considering the aforedescribed acoustic core to be a primary scanning location on a notional inner or outer scanning ring and proceeding to develop acoustic cores at each of the other primary (and any necessary secondary) scanning locations of such outer and inner scanning rings.

I claim:

1. A method for investigating sub-surface acoustical properties of a layered site, comprising the steps of:
   (a) selecting a plurality of primary scanning locations at a site;
   (b) generating at least one sonic pulse for calculating the speed of sound in water at said scanning locations;
   (c) for each scanning location, undertaking at least once the sub-steps of:
      (i) selecting a power, resultant center frequency, beamwidth, bandwidth, shape and incident angle for an input signal, said incident angle chosen so that a significant portion of the energy in the input signal will enter the site;
      (ii) insonifying said scanning location with said input signal;
      (iii) receiving reflected signals; and
      (iv) predicting sub-surface acoustical properties of layers of said site at said scanning location from said reflected signals and said at least one sonic pulse.

2. The method of claim 1 wherein sub-step (c) (iv) comprises iteratively predicting the acoustical properties of adjacent layers at said site, in turn, commencing with the surface layer at said site.

3. The method of claim 2 wherein said scanning locations fall on two notional concentric scanning rings and wherein said primary scanning locations are equally spaced about the circumference of each of said two concentric scanning rings.

4. The method of claim 3 including the steps of:
   (d) determining the coherence of predicted acoustical properties of a layer between each pair of adjacent scanning locations on a scanning ring; and
   (e) where the coherence of a pair of adjacent scanning locations falls below a pre-set bound, selecting at least one secondary scanning location between said pair of adjacent locations and for each said secondary scanning location, undertaking step (c).

5. The method of claim 4 wherein a radial line intersecting one of said primary scanning locations on one of said two notional concentric scanning circles, intersects a second one of said primary scanning locations on the other of said two notional concentric scanning circles.

6. The method of claim 5 wherein, for each scanning location, the sub-steps of step (c) are repeated for a selected incident angle for an input signal with a different selection of one or more of power, resultant centre frequency, beamwidth, shape, and bandwidth for said input signal if the intensity of reflected signal falls below a pre-set bound.

7. The method of claim 1 wherein the acoustical properties predicted comprise:
   the velocity of sound propogation; and
   the attenuation of sound; the property of reflectivity and of backscatter.

8. Apparatus for determining sub-surface acoustical properties at a layered seabed site comprising:
   (a) a stationary platform for resting on the seabed proximate a layered seabed site;
   (b) transducer input signal means comprising variable shape pulse generator means, variable amplitude and frequency carrier wave generator means, and mixer means for forming an amplitude modulated acoustic pulse;
   (c) transducer means moveably supported by said platform and responsive to said transducer input signal means for operating while submersed and for insonifying scanning locations at said layered seabed site with an insonifying signal;

(d) receiver means moveably supported by said platform for receiving signals reflected from said layered seabed site; and (e) processor means for determining acoustic properties of layers of said seabed site at said scanning locations from the characteristics of said insonifying signals and said reflected signals.

9. The apparatus of claim 8 wherein the transducer is operated in a parametric mode wherein the carrier frequency for the transducer means is about 100 kHz, the height of the transducer means above the seabed is about 8.5 m and the transducer area is about 1.2 m$^2$.

10. The apparatus of claim 8 wherein said processor means is also for determining the coherence of acoustic properties in a layer between adjacent scanning locations and for selecting at least one additional scanning location if said coherence falls below a pre-set bound.

11. The apparatus of claim 8 wherein the transducer is operated in a parametric mode wherein the carrier frequency (f) for the transducer means is equal to $885918/l$ H$_z$ where l is the height of the transducer means above the seabed, the square of the height of the transducer means above the seabed ($l^2$) is equal to $W/53.19$ W, where W is the power radiated by the transducer means and is equivalent to $\pi a^2 \cdot 10^4$ W where a is the radius of the transducer means and the radius of the transducer means (a) is greater than or equal to $\sqrt{l/f}$.

* * * * *